(12) United States Patent
Perot et al.

(10) Patent No.: US 8,939,942 B2
(45) Date of Patent: Jan. 27, 2015

(54) NEEDLE PROTECTION ASSEMBLY

(75) Inventors: Frederic Perot, Saint Paul de Varces (FR); Laurent Barrelle, Saint Nizier du Moucherotte (FR); Kevin David Neale, Swindon (GB); Bruno Baney, Claix (FR); Paul Holloway, Cirencester Glos (GB)

(73) Assignee: Becton Dickinson France, Le Pont de Claix (FR)

( * ) Notice: Subject to any disclaimer, the term of this patent is extended or adjusted under 35 U.S.C. 154(b) by 840 days.

(21) Appl. No.: 12/988,366

(22) PCT Filed: Apr. 14, 2009
(Under 37 CFR 1.47)

(86) PCT No.: PCT/IB2009/005523
§ 371 (c)(1),
(2), (4) Date: Mar. 28, 2011

(87) PCT Pub. No.: WO2009/144547
PCT Pub. Date: Dec. 3, 2009

(65) Prior Publication Data
US 2011/0270198 A1    Nov. 3, 2011

(30) Foreign Application Priority Data

Apr. 16, 2008  (FR) ...................... 08 02102

(51) Int. Cl.
*A61M 5/32*  (2006.01)
*A61M 5/00*  (2006.01)

(52) U.S. Cl.
CPC ............. *A61M 5/326* (2013.01); *A61M 5/3272* (2013.01); *A61M 2005/3247* (2013.01); *A61M 2005/3267* (2013.01)

USPC ........................................... 604/198; 604/110

(58) Field of Classification Search
USPC .............................. 604/110, 164.08, 192, 198
See application file for complete search history.

(56) References Cited

U.S. PATENT DOCUMENTS

| 4,813,940 | A |   | 3/1989 | Parry |
| 4,932,947 | A | * | 6/1990 | Cardwell ...................... 604/198 |
| 5,415,645 | A | * | 5/1995 | Friend et al. .................. 604/110 |
| 5,429,612 | A | * | 7/1995 | Berthier ........................ 604/198 |
| 5,527,294 | A | * | 6/1996 | Weatherford et al. ........ 604/198 |
| 5,549,558 | A | * | 8/1996 | Martin .......................... 604/110 |

(Continued)

FOREIGN PATENT DOCUMENTS

| EP | 1 447 108 A1 | 8/2004 |
| WO | 2004000397 A1 | 12/2003 |

(Continued)

*Primary Examiner* — Kevin C Sirmons
*Assistant Examiner* — William Carpenter
(74) *Attorney, Agent, or Firm* — Hoffmann & Baron, LLP

(57) ABSTRACT

The application relates to a needle protection assembly (1) comprising:—a supporting element (18) and a needle shield (8),—one locking element (20) located within said needle protection assembly (1) and not accessible to the user,—urging means (24) for displacing said needle shield (8),—a peg (19) located on said supporting element (18) or on said needle shield (8), and a cam (9) located on said needle shield (8) or on said supporting element (18), and—said locking element (20) is not formed by said peg (19) and cam (9). The respective longitudinal axis of the needle shield (8) and of the locking element (20) are merged when said needle shield (8) is in its before use or in use positions, and they form an angle (a) when said needle shield (8) is in its after use position.

13 Claims, 11 Drawing Sheets

(56) References Cited

U.S. PATENT DOCUMENTS

Figure 1:
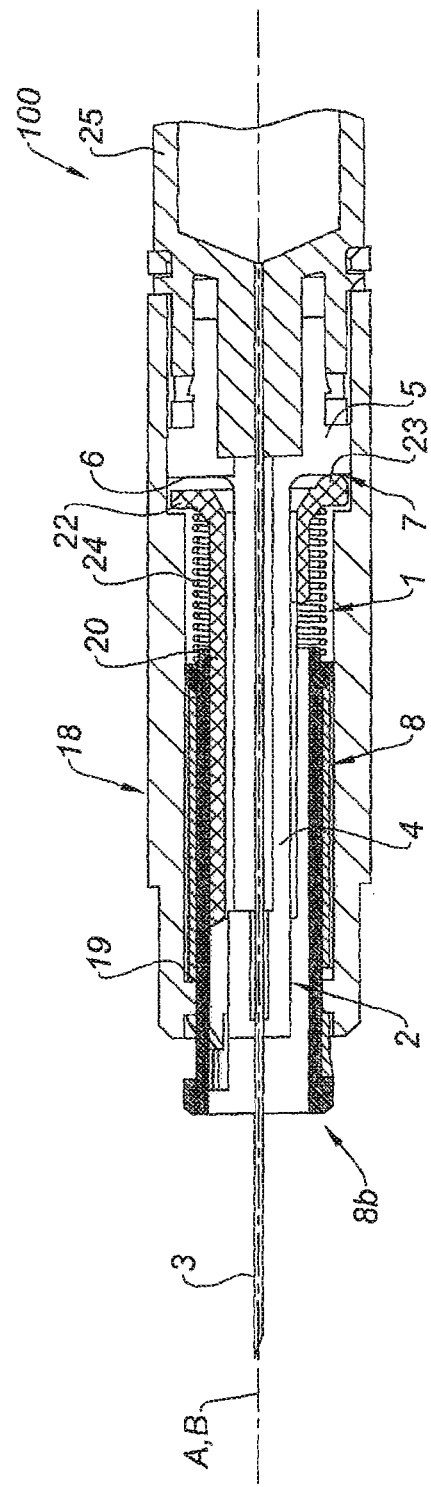

| | | | |
|---|---|---|---|
| 5,562,624 A * | 10/1996 | Righi et al. | 604/110 |
| 5,601,535 A * | 2/1997 | Byrne et al. | 604/198 |
| 5,688,241 A * | 11/1997 | Asbaghi | 604/110 |
| 2003/0014018 A1* | 1/2003 | Giambattista et al. | 604/198 |
| 2005/0004551 A1* | 1/2005 | Barrelle | 604/506 |
| 2005/0113750 A1 | 5/2005 | Targell | |
| 2005/0165353 A1* | 7/2005 | Pessin | 604/110 |
| 2006/0069353 A2* | 3/2006 | Barrelle et al. | 604/198 |
| 2006/0189933 A1* | 8/2006 | Alheidt et al. | 604/110 |

FOREIGN PATENT DOCUMENTS

| | | |
|---|---|---|
| WO | 2004071560 A1 | 8/2004 |
| WO | WO 2006131832 A1 * | 12/2006 |

* cited by examiner

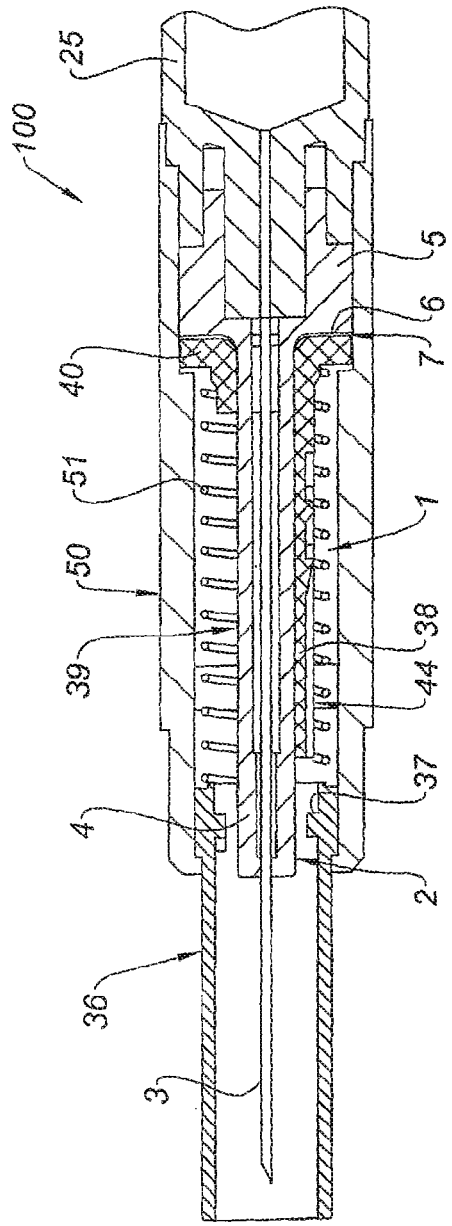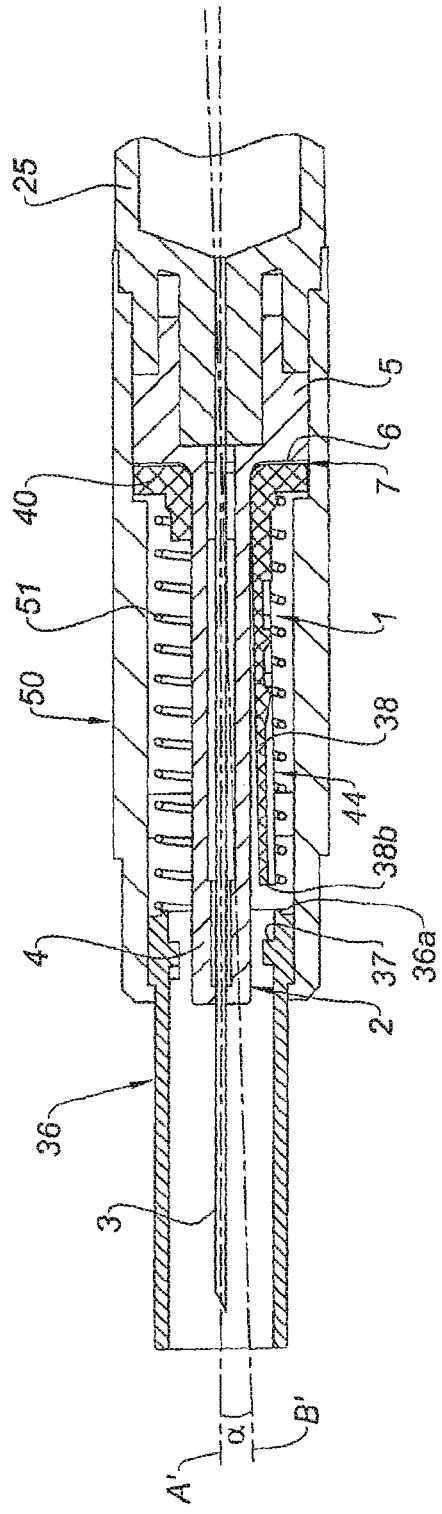

NEEDLE PROTECTION ASSEMBLY

The present invention relates to a needle protection assembly that is to be connected to an injection device such as a syringe in view of completing an injection, said needle protection assembly being triggered after the injection in order to protect the user from accidental needle stick injuries and prevent needle re-use.

In this application, the "distal end" of a component or of a device is to be understood as meaning the end furthest from the user's hand and the "proximal end" is to be understood as meaning the end closest to the user's hand. Likewise, in this application, the "distal direction" is to be understood as meaning the direction of injection, and the "proximal direction" is to be understood as meaning the opposite direction to the direction of injection.

In the medical field, it is usual to provide injection devices with needle protection systems in order to prevent the needle to be reached by the user or the patient before and/or after use of the injection device, in view of limiting accidental needle stick injuries. In addition, such needle protection systems also enable to prevent re-use of the injection devices.

Usually, the needle protection systems include a needle shield able to move distally over the needle once the injection is completed. The distal movement of the needle shield with respect to the needle is often triggered by a spring in an automatic way when the needle is withdrawn from the injection site. In general, the needle shield is then locked in its "after use" position thanks to a locking system, most of the time based on the cooperation of deflecting members located either on the needle hub and/or on the needle shield.

The document US2005/0113750 discloses such a needle protection system in which the locking system comprises a spring urging a needle shield toward its "after use" position and a deflecting leg provided on the needle shield, the deflecting leg being engaged into a groove provided on the needle hub in the "after use" position. US2003/0014018 also discloses a needle protection system in which the locking system comprises a spring urging a needle shield toward its "after use" position and deflecting legs;

Nevertheless, the needle protection systems of the prior art have the drawback that, because of the energy necessary to deflect the deflecting members, the spring force must be high in order to displace the needle shield and overcome the deflecting members resistance. This has the consequence that, in storage position, before use, the high spring force of the compressed spring may deform the usual plastic parts forming the needle assembly and/or the injection device. This deformation may cause the needle protection system not to work properly at the time of use. This deformation may also cause wrong depth injection at the time of the injection. Indeed, during the injection, the high spring force will push the needle shield against the skin, generating a push back force on the injection device proportional with the high force of the spring. This push back force will render difficult and unpredictable the accurate positioning of a constant pressure on the skin and make the injection operation more difficult to perform. In addition, springs with high force are more cumbersome, expensive and difficult to assemble than low duty spring. On the other side, low duty springs do not apply enough force to be able to overcome the deflecting members resistance and allow the needle protection system to work properly.

WO2005/044349 discloses a needle protection system in which the locking system comprises a spring urging a needle shield toward its "after use" position and an arm provided with a pin, the pin having to overcome a blocking element before coming engaged into a groove provided on the needle hub in the "after use" position. Once again, the device of WO2005/044349 requires a spring with a high force in order for the pin to overcome the resistance of the blocking element.

EP 1 447 108 discloses a needle protection system in which the locking system comprises cantilever arms.

US2005/0277893 discloses a needle shield that becomes misaligned with the needle hub in its "after use" position. Nevertheless, in the device of US2005/0277893, the needle is not guided between a "before use" position and the "in use" position and in the case where the needle is flexible, it is difficult to perform a safe and controlled injection. In addition, in US2005/0277893, the needle is not visible in the "before use" position of the device. It is therefore difficult for a user to determine whether the device is in its "before use" position or in its "after use" position and when the "in use" position is reached.

Moreover, the needle protection systems of the prior art necessitate a plurality of different parts, in particular several parts forming the locking system, and the needle protection systems are therefore difficult and long to manufacture.

There is therefore a need for a needle protection assembly that would be easily triggered at the end of the injection in order to avoid accidental needle stick for the user and prevent the re-use of the needle. There is at the same time a need for a needle protection assembly that would not be likely to cause the deformation of the plastic parts forming the needle protection assembly during storage, that would be easy to assemble, and that would be user friendly. In addition, there is a need for a needle protection assembly that allows the needle to be visible and to be guided, for example from a "before use" position in which only a part of the needle is visible, and an "in use" position in which the needle is uncovered on its usable length for the injection.

The present invention remedies to this problem by providing a needle protection assembly comprising both a specific locking system so that the urging means, such as a spring, used to cause the distal movement of the protection at the end of the injection is a low duty urging means that does not need to show a too high force, and a specific positioning system allowing the needle to be visible before use, and to be guidable, for example from the "before use" position to the "in use" position, so that it is easy for the user to operate the system between the "before use", "in use" and the "after use" positions.

A first aspect of the invention is a needle protection assembly intended to protect the needle of a needle assembly, said needle protection assembly comprising at least a supporting element and a needle shield, said needle shield being axially movable with respect to said supporting element between an "in use" position in which said needle shield is intended to leave an "in use" portion of said needle uncovered, and an "after use" position distally spaced apart from said "in use" position" and in which said needle shield is intended to cover said needle, said needle protection assembly further comprising:
  at least one locking element located within said needle protection assembly and not accessible to the user, said locking element being movable between at least a "free" position, in which said needle shield can be moved at least from its "in use" position to its "after use" position, and a "locking" position in which said locking element prevents said needle shield from moving back from its "after use" position in the proximal direction,
  urging means intended to displace said needle shield from its "in use" position to its "after use" position, a peg located on said supporting element or on said needle shield, and a cam located respectively on said needle shield or on said supporting element, said peg being movable within said cam so as to define said "in use" and "after use" positions, upon increased or released distal pressure exerted by the user on said needle protection assembly, and said locking element being not formed by said peg and said cam, characterized in that said needle shield having a longitudinal axis (A; A'), said locking element has a general longitudinal shape having a longitudinal axis (B; B'), the longitudinal axis (A; A') of the needle shield and the longitudinal axis (B, B') of the locking element are merged when said needle shield is in its "in use" positions, said longitudinal axis (A; A') of the needle shield forms an angle ($\alpha$; $\alpha'$) with the longitudinal axis (B; B') of the locking element when said needle shield is in its "after use" position.

In the present application, by "merged" is meant that the longitudinal axis A, respectively A', and B, respectively B', are coaxial, they are identical.

In the present application, by "form an angle" is meant that the longitudinal axis A, respectively A', and B, respectively B', are no more coaxial, they intersect and form an angle which is different than 0°, 180° or 360°.

In an embodiment of the invention, said needle shield is axially movable between a "before use" position, in which said needle shield leaves a "before use" portion of the needle uncovered, said "in use" portion being greater than said "before use" portion, and said "in use" position. The peg and cam may also define the "before use" position.

In the needle protection assembly of the invention, the urging means, for example a spring, is used to cause the movement of the needle shield once the injection is completed but it does not have to overcome the friction force opposed by deflecting members of the locking systems of the prior art or any point of resistance to lock the needle shield in its "after use" position. It is the fact that the needle shield and the locking element are displaced one with respect to the other, for example, they are no more coaxial and form an angle, in the "after use" position of the needle shield, that locks the needle shield in said "after use" position. Less force is required from the urging means, such as the spring, of the needle protection assembly of the invention. In consequence, the urging means of the assembly of the invention, even in the "storage" position or in the "before use" position, does not exert a high force on the plastic parts forming the assembly. The risks of deformation of these plastic parts are therefore limited with the needle protection assembly of the invention. In addition, a weaker spring than the springs used in the devices of the prior art may be used as urging means in the needle protection assembly of the invention.

The needle protection assembly of the invention is therefore easier to manufacture than assemblies of the prior art. The needle protection assembly of the invention, because it requires less manufacturing parts, is also environment friendly.

The needle protection assembly of the invention allows the needle to be visible in the "before use" position of the assembly. Moreover, the needle is guided from the "before use" position to the "in use" position: the needle is therefore rendered more rigid during this step and the injection is safer. The needle protection assembly is therefore of easier use for the user who can see the needle and who can easily determine where to prick. Moreover, the needle protection assembly of the invention is provided with a positioning system allowing the user to know when the needle protection assembly is in its "before use" position, in its "in use" position and in its "after use" position.

Moreover, the locking element of the needle protection assembly of the invention is not accessible for the user. The user can therefore not put the needle shield back in its "in use" position once said needle shield has reached its "after use" position. The needle protection assembly of the invention is therefore particularly safe.

In an embodiment of the invention, said cam includes at least a first and a second longitudinal tracks, both having a globally longitudinal shape and joining at an intersection via their respective proximal ends, respectively via their respective distal ends, said peg being located at an "initial" position in said first track when said needle shield is in its "before use" position, and said peg being located at a "final" position in said second longitudinal track or beyond said second longitudinal track, when said needle shield is in said "after use" position, said "final" position of the peg being distally, respectively proximally, spaced with respect to said "initial" position.

Said peg may be located at said intersection of the first and second longitudinal tracks when said needle shield is in its "in use" position.

In an embodiment of the invention, said cam is provided with an inclined surface at the vicinity of the intersection of said first and second longitudinal tracks, said inclined surface urging said peg in the second longitudinal track when said needle shield moves from its "in use" position to its "after use" position.

In an embodiment of the invention, said supporting element is an outer sleeve receiving both said needle shield and said locking element.

In an embodiment of the invention, said supporting element forms at least part of said locking element.

Said locking element may have the global shape of a tube provided at its proximal end with an asymmetrical outer flange. Preferably, said outer flange is provided with a proximal inclined surface. Said outer flange may be provided with one projection extending proximally.

In an embodiment of the invention, said urging means comprise at least a helical spring.

Another aspect of the invention is a needle assembly comprising at least a needle hub provided with a needle wherein it further comprises a needle protection assembly as described above. Said supporting element may comprise said needle hub.

Another aspect of the invention is an injection device comprising at least a needle assembly and a reservoir, wherein it further comprises a needle protection assembly as described above.

Figure 2:
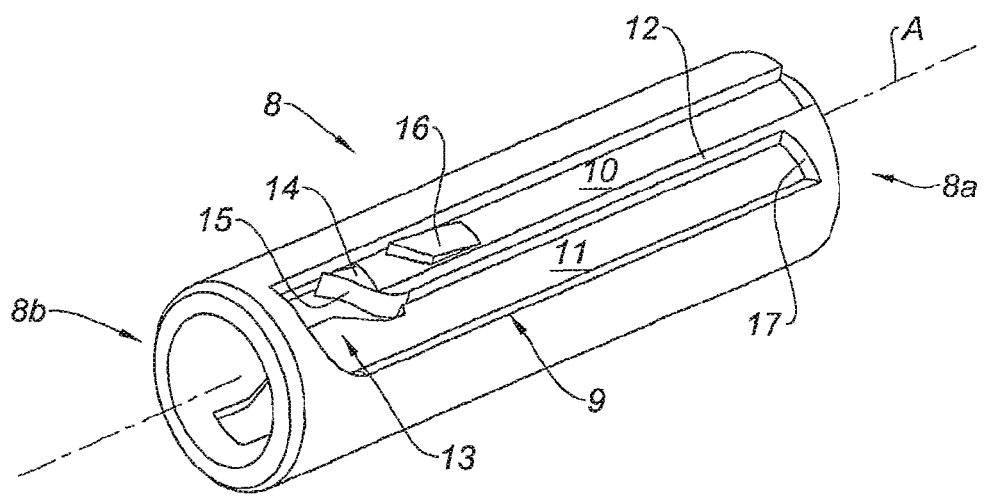
Figure 3:
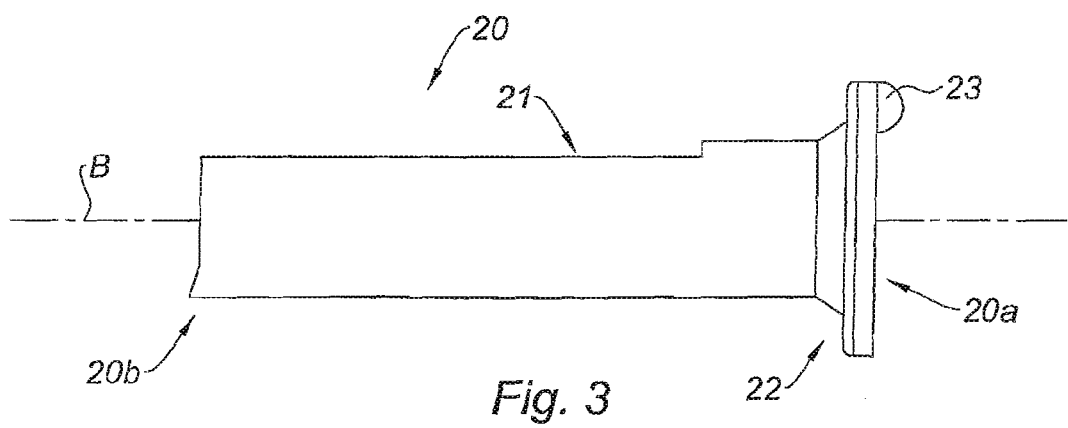
Figure 4:
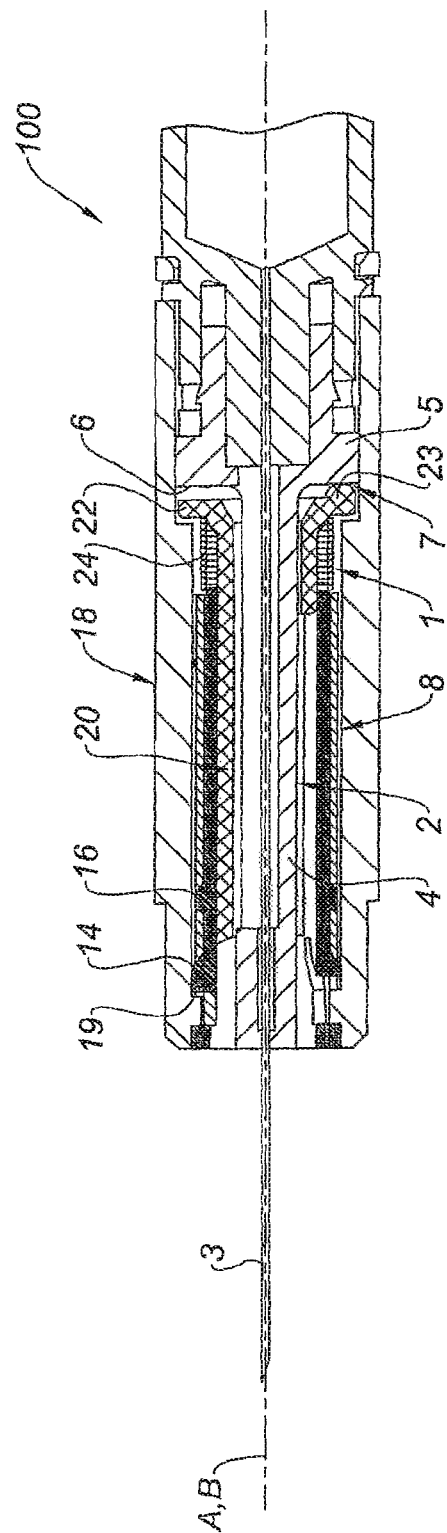
Figure 5:
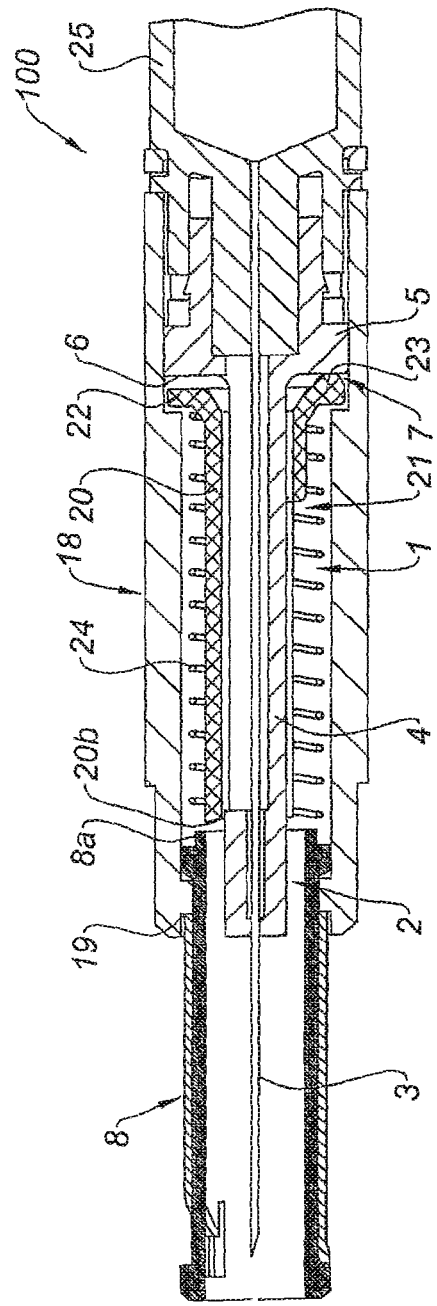
Figure 6:
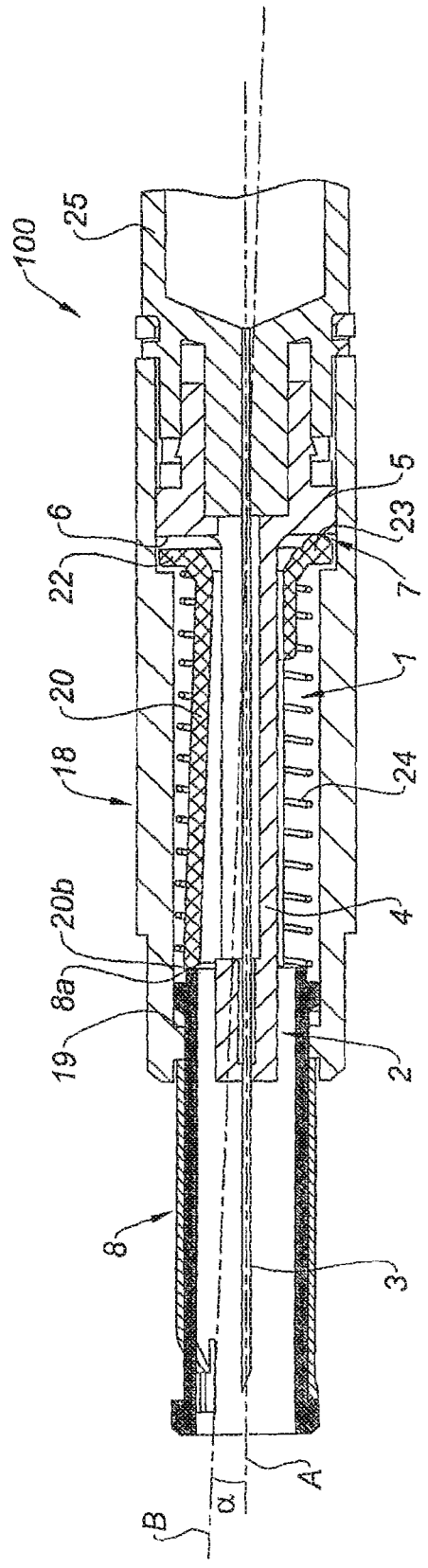

The needle protection assembly of the invention will now be further described in reference to the following description and attached drawings in which:

FIG. 1 is a partial cross section view of an injection device comprising a needle protection assembly according to the invention, in the "before use" position, FIG. 2 is a perspective view of the needle shield of the needle protection assembly of FIG. 1, FIG. 3 is a side view of the locking element of the needle protection assembly of FIG. 1, FIG. 4 is a partial cross section view of the injection device of FIG. 1 in the "in use" position, FIG. 5 is a partial cross section view of the injection device of FIG. 1 when the needle shield reaches its "after use" position, FIG. 6 is a partial cross section of the injection device of FIG. 1 when the needle shield is locked in its "after use" position.

Figure 7:
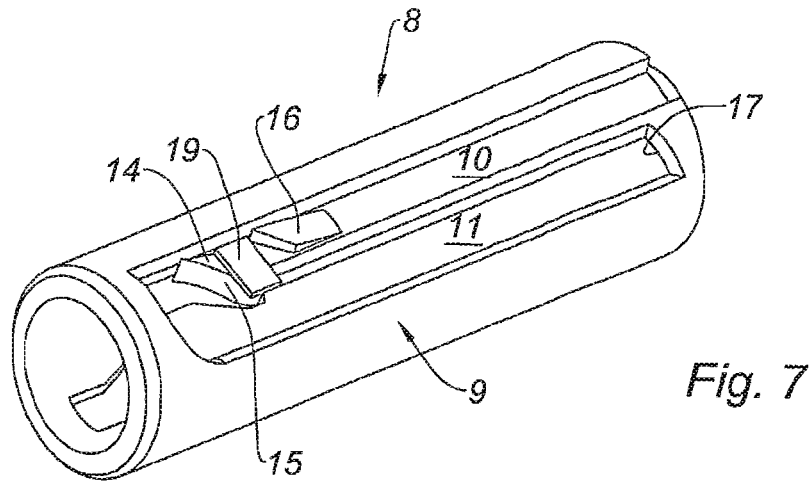
Figure 8:
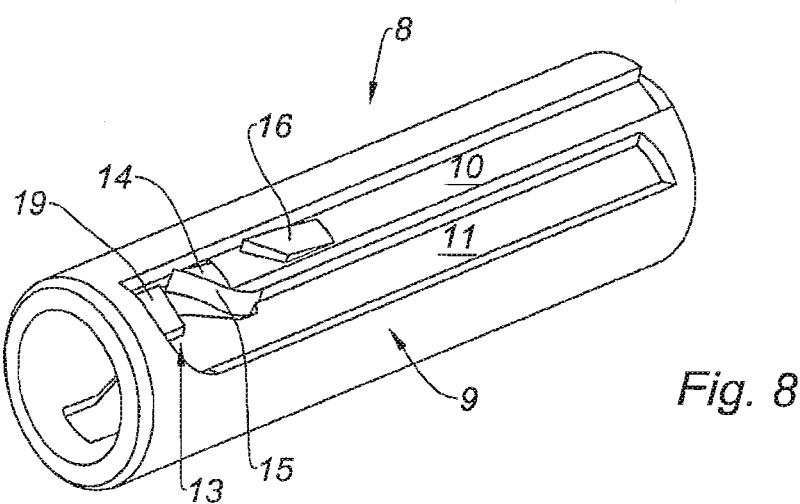
Figure 9:
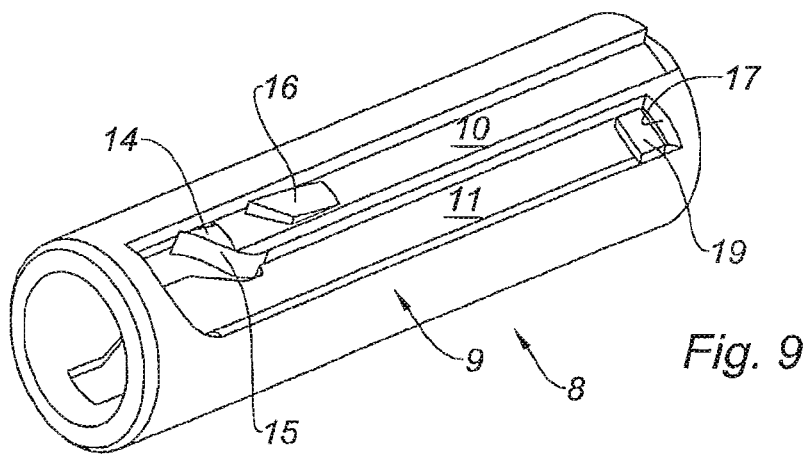
Figure 10:
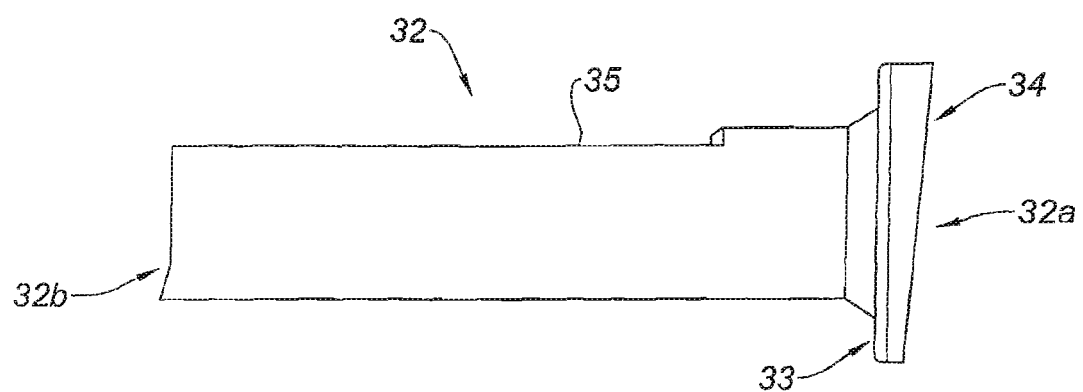
Figure 11:
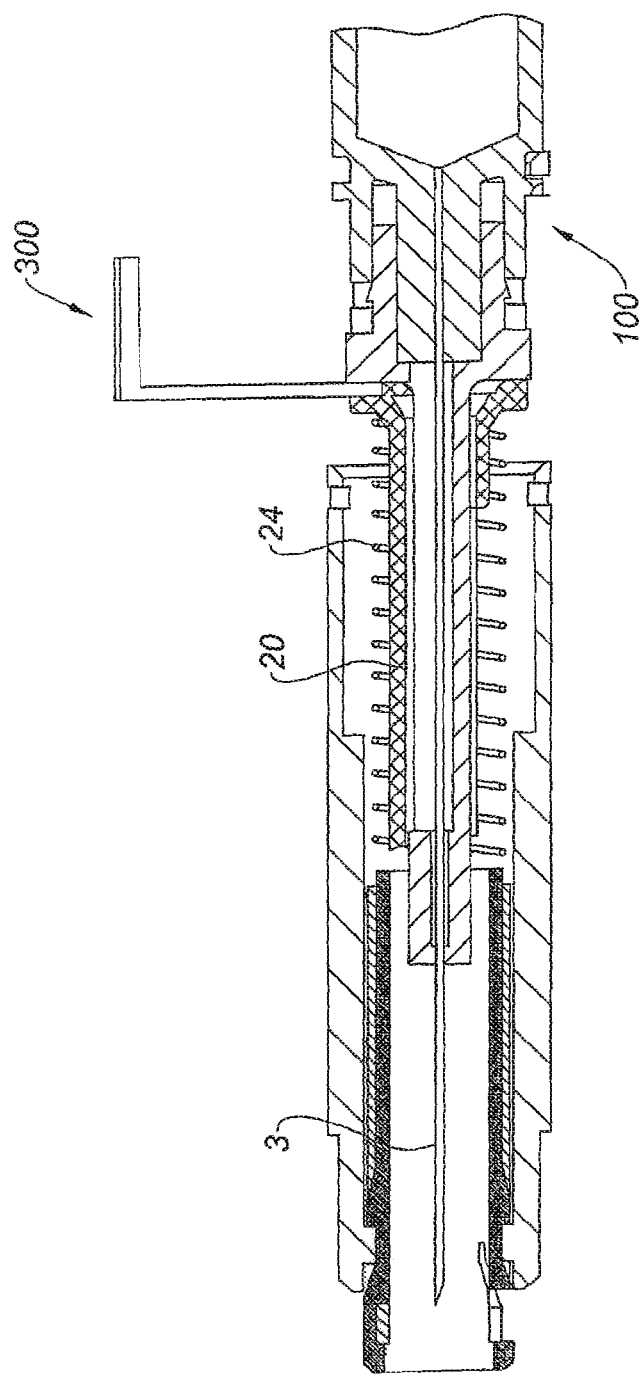
Figure 13:
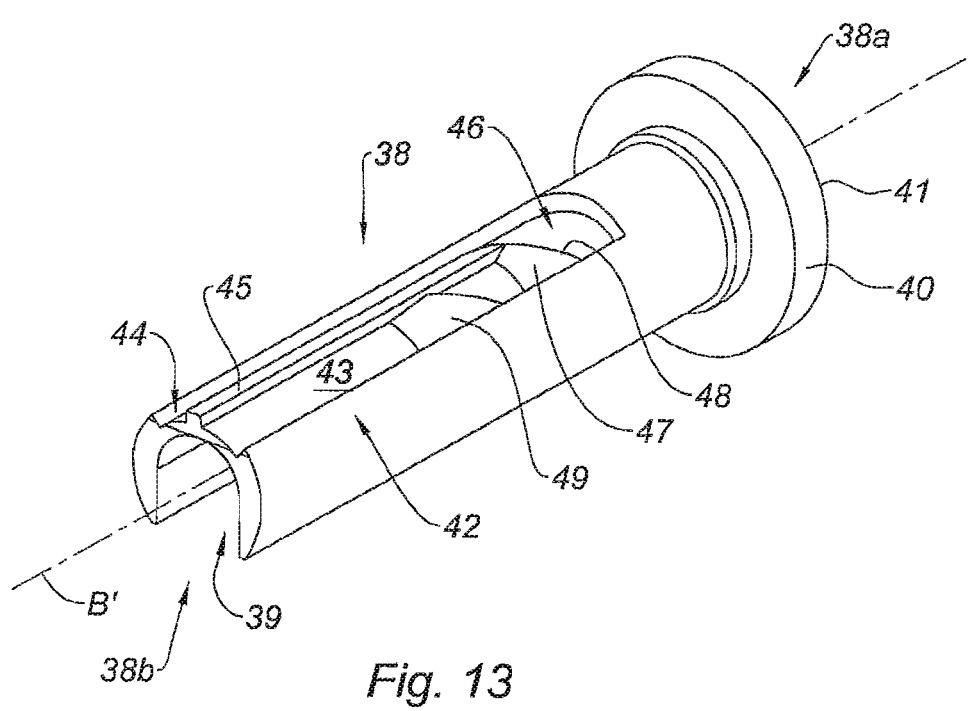
Figure 14:
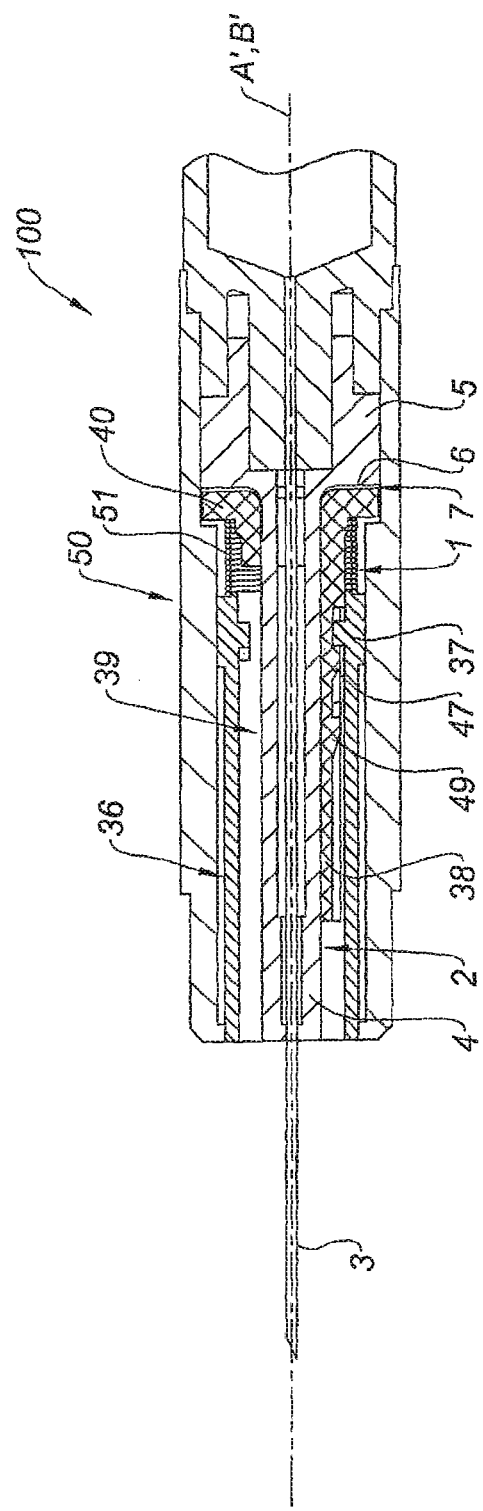

FIGS. 7 to 9 are partial views of the needle protection assembly of the injection device of FIGS. 1-6 showing the peg position in the cam, respectively in the following positions: "before use", "in use" and "after use", FIG. 10 is a side view of an alternative embodiment of a locking element of a needle protection assembly of the invention, FIG. 11 is a partial cross section view of the injection device of FIG. 1-6 showing assembly of the locking element and urging means, FIG. 12 is a partial cross section view of an injection device comprising an alternative embodiment of a needle protection assembly according to the invention, in the "before use" position, FIG. 13 is a perspective view of the locking element of the needle protection assembly of FIG. 12, FIG. 14 is a partial cross section view of the injection device of FIG. 12 in the "in use" position of the needle shield.

Figure 12:
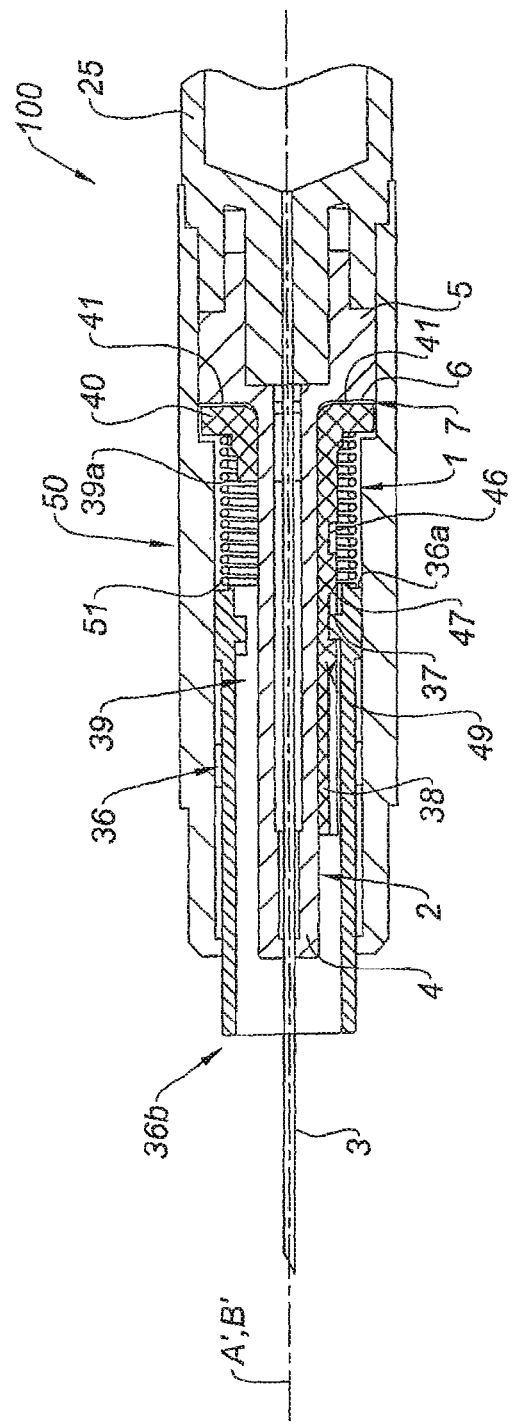

FIG. 15 is a partial cross section view of the injection device of FIG. 12 when the needle shield reaches its "after use" position, FIG. 16 is a partial cross section view of the device of FIG. 12 when the needle shield is locked in its "after use" position.

In the following description, the needle protection assembly of the invention has at least two positions:

- an "in use" position during which the injection device is applied against the injection site, the user exerts a distal pressure on the injection device, the needle is inserted in the injection site and is not covered by the needle shield: in this "in use" position, the needle is uncovered by the needle shield on an "in use" portion corresponding to its usable length, that is to say its length necessary to penetrate the patient's kin to perform the injection at the right injection depth;
- an "after use" position after withdrawal of the needle from the injection site, in which the user does not exert any more any distal pressure on the injection device: in this "after use" position, the needle shield covers the needle.

Preferably, the needle protection assembly of the invention has also a "before use" position, before proper use of the injection device bearing the needle protection assembly of the invention; in this "before use" position the needle is at least partly uncovered by the needle shield on a "before use" portion, the "in use" portion in the "in use" position being greater than the "before use" portion in the "before use" position, the needle being therefore visible in the "before use" position by the user who does not yet exert any distal pressure on the injection device and who can properly adjust where the needle is to be inserted in the skin.

In reference to FIG. 1 is shown a needle protection assembly 1 according to the invention, in the "before use" position, mounted on an injection device 100 (partially shown). The needle protection assembly 1 of the invention comprises a support 2 that bears a needle 3. The support 2 comprises an inner core 4, and a proximal part 5 of outer diameter larger than the outer diameter of the inner core 4 and forming with respect to said inner core 4 a rim 6. The rim 6 defines a distal plane surface 7 perpendicular to the longitudinal axis of the support 2.

The needle protection assembly 1 of FIG. 1 also comprises a needle shield 8 receiving at least partially said support 2 and in particular said inner core 4 of said support 2. With reference to FIG. 2, the needle shield 8 has the global shape of a tube having a longitudinal axis A. The needle shield 8 is open at its proximal end 8a and at its distal end 8b. The outer wall of the needle shield 8 is provided with a cam 9. The cam 9 comprises a first longitudinal track 10 and a second longitudinal track 11 substantially parallel to each other and separated by a separation wall 12. The first and second longitudinal tracks (10, 11) are joined at their respective distal ends via an intersection 13. In the vicinity of the intersection 13, the first longitudinal track 10 is provided with a ramp 14, the distal end of which is provided with an inclined surface 15, the inclined surface 15 facing the second longitudinal track 11. In addition, the first longitudinal track 10 is provided with a step 16, located proximally with respect to said ramp 14. The proximal end of the second longitudinal track 11 is provided with a stop wall 17.

With reference to FIG. 1, the needle protection assembly 1 of FIG. 1 further comprises a supporting element under the form of an outer sleeve 18 which receives the needle shield 8. The outer sleeve 18 is provided in the distal region of its inner wall with at least a peg 19.

As will appear clearly from the description of FIGS. 1-6, the needle shield 8 is axially movable with respect to the outer sleeve 18 between a "before use" position, in which said needle is uncovered by the needle shield 8 on a "before use" portion, the needle 3 being visible by the user as shown on FIG. 1, an "in use" position in which said needle shield 8 leaves an "in use" portion of said needle 3 uncovered, the "in use" portion being greater than the "before use" portion, as shown on FIG. 4, and an "after use" position in which said needle shield 8 covers said needle 3, as shown on FIG. 5.

The needle protection assembly 1 of FIG. 1 further comprises a tube 20 surrounding the inner core 4 of the support 2, said tube 20 being partly received within said needle shield 8. The tube 20 is also received within the supporting element or outer sleeve 18. With reference to FIG. 3, the tube 20 has a longitudinal axis B and is open at its proximal end 20a and at its distal end 20b. As appears on FIG. 3, a part of the wall of the tube 20 has been cut on a part of its length along a longitudinal plane, thereby defining a longitudinal cut 21 extending from a point located distally with respect to the proximal end 20a of the tube 20 up to the distal end 20b of the tube 20. The tube 20 is provided at its proximal end 20a with an outer flange 22, said outer flange 22 being provided on its proximal face and substantially in alignment with the longitudinal cut 21 with one projection 23 extending proximally. The outer flange 22 is therefore asymmetrical. On the example shown, the projection 23 has a semi-spherical shape.

With reference to FIG. 1, in the "before use" position of the needle shield 8, the tube 20 is received within the needle shield 8 and the proximal face 20a of the tube 20 bears on the distal plane surface 7 defined by the rim 6 of the support 2 by means of the semi-spherical projection 23 of the outer flange 22 of the tube 20. As appears also from FIG. 1, in this position, the tube 20 is maintained coaxial with the needle shield 8 because it is surrounded by the needle shield 8 which is tubular. In consequence, the respective longitudinal axis A and B of the needle shield 8 and of the tube 20 are merged but part of the proximal face of the outer flange 22 which is diametrically opposed to the projection 23 does not contact the distal plane surface 7 of the rim 6 as is shown on FIG. 1. As a remark, on this figure, the longitudinal axis A and B are also merged with the longitudinal axis of the injection device 100. In other words, the needle shield 8 and the tube 20 are in alignment with each other.

The needle protection assembly 1 of FIG. 1 further comprises a helical spring 24, located between the needle shield 8 and the tube 20. On the example shown on FIG. 1, the proximal end of the helical spring 24 bears on the distal face of the outer flange 22 of the tube 20 and its distal end bears on the proximal end of the needle shield 8. In the "before use" position shown on FIG. 1, the helical spring 24 is in a partially expanded state. As will appear later in the detailed description of the operation of the injection device 100, the helical spring 24 acts as urging means for displacing the needle shield 8 from its "in use" position to its "after use" position.

The injection device 100 of FIG. 1 also comprises a barrel 25 (partially shown) intended to receive a product to be injected and said barrel 25 being fixed to said outer sleeve 18 and to the support 2 bearing the needle 3.

The operation of the needle protection assembly 1 and of the injection device 100 will now be explained in reference to FIGS. 1 to 9.

On FIG. 1, the needle protection assembly 1 is in a "before use" position. In this "before use" position shown on FIG. 1, the needle shield 8 covers part of the needle 3. Therefore, the needle 3 is visible for the user. The user can prick the needle 3 in the site of injection.

In this "before use" position shown on FIG. 1, as shown on FIG. 7, the peg 19 of the outer sleeve 18 is in an initial position located between the ramp 14 and the step 16 of the first track 10 of the cam 9 of the needle shield 8. On FIGS. 7-9, for sake of clarity, only the peg 19 of the outer sleeve 18 is shown. One must understand that the peg 19 is part of the outer sleeve 18 (not shown) which surrounds the needle shield 8, as shown on FIG. 1. The proximal movement of the peg 19 is therefore prevented by the step 16.

In this "before use" position shown on FIG. 1, the longitudinal axis A of the needle shield 8 and the longitudinal axis B of the tube 20 are merged, ie coaxial. The needle shield 8 and the tube 20 are in alignment with each other.

The user then applies the injection device 100 on the skin of a patient (not shown), inserts the needle 3 into the injection site until the distal end 8b of the needle shield 8 comes in contact with the skin. In order to fully insert the needle 3 in the site of injection, the user then exerts a distal pressure on the injection device 100, this having as a consequence to cause the distal movement of the outer sleeve 18 with respect to the needle shield 8, as shown on FIG. 4, said needle shield 8 being blocked against the skin of the patient (not shown). During the distal movement of the outer sleeve 18, the support 2, which is fixed to the outer sleeve 18, has also moved distally and has pushed the tube 20 in the distal direction via the rim 6 contacting the projection 23 of the outer flange 22 of the tube 20. The needle shield 8 being stopped against the skin of the patient, the helical spring 24 is now in a more compressed state than in the "before use" position, as shown on FIG. 4. As shown on FIG. 8, during the distal movement of the outer sleeve 18, the peg 19 has overcome the ramp 14 and is now in abutment against the proximal face of the intersection 13 of the first and second longitudinal tracks (10, 11) of the cam 9. The needle shield 8 is now in its "in use" position. The user may then realize the injection of the product to be injected.

In this "in use" position of the needle shield 8 as shown on FIG. 4, the longitudinal axis A of the needle shield 8 and the longitudinal axis B of the tube 20 are merged. The needle shield 8 and the tube 20 are in alignment with each other.

Once the injection step (not shown) is completed, the user removes the injection device 100 from the injection site and the needle shield 8 is no more blocked by the skin of the patient. The helical spring 24 is therefore free to return to its expanded state and it causes the distal movement of the needle shield 8 with respect to the support 2 and to the outer sleeve 18 as shown on FIG. 5.

As shown on FIG. 9, the peg 19 of the outer sleeve 18 has been guided into the second longitudinal track 11 of the cam 9 by the inclined surface 15. The peg 19 has then travelled along the second longitudinal track 11 until it has reached the stop wall 17 at the proximal end of said second longitudinal track 11 where said peg 19 reaches its final position, corresponding to the "after use" position of the needle shield 8, as shown on FIG. 5. The final position of the peg 19 is therefore proximally spaced with respect to its initial position.

The needle shield 8 therefore deploys and covers the needle 3, thereby preventing any accidental needle stick injury for the user and any re-use of the injection device 100. During this step, the helical spring 24 acts as urging means tending to displace the needle shield 8 from its "in use" position to its "after use" position.

While expanding, the helical spring 24 has pushed the needle shield 8 distally beyond the tube 20 which is then no more surrounded by the needle shield 8, as shown on FIG. 5, at the moment the needle shield 8 reaches its "after use" position". In consequence, the tube 20 is no more maintained coaxial with the needle shield 8: thanks to the longitudinal cut 21 and to the semi-spherical projection 23 rotating on itself, the tube 20 naturally cants, as shown on FIG. 6 and its distal end 20b comes in regard to the proximal end 8a of the needle shield 8. The tube 20 is no more coaxial with the needle shield 8. This can be seen on FIG. 6 on which the longitudinal axis A of the needle shield 8 and the longitudinal axis B of the tube 20 intersect and are now forming an angle α. The tube 20 therefore acts as a locking element of the needle shield 8 and is in a "locking position" when the needle shield 8 is in its "after use" position. As is visible from FIGS. 1 and 4, in the, "before use" and "in use" positions of the needle shield 8, the tube 20 remained coaxial with the needle shield 8 and did not prevent movement of said needle shield 8 from a position to the other. On these FIGS. 1 and 4, the locking element formed by the tube 20 was in a "free position". As appears clearly from the above description, the locking element, namely the tube 20, is in no way accessible to the user, whatever the position of the needle shield 8. The needle protection assembly of the invention is therefore particularly safe.

In the needle protection assembly 1 and the injection device 100 of the invention, the force of the helical spring 24 of the needle protection assembly 1 and the injection device 100 of the invention does not need to be high because it does not have to overcome any flexible locking member. In consequence, when the needle protection assembly 1 and the injection device 100 of the invention are in a "before use" position, as shown on FIG. 1, the force exerted by the spring 24 on the different parts forming the needle protection assembly 1 and/or the injection device 100 is not high and does not deform said parts. The spring 24 is not cumbersome and the needle protection assembly 1 and/or the injection device 100 can have moderate size. In addition, the spring 24 is easy to assemble because it requires less pressure to be compressed thane high force spring.

Moreover, as appears from the description of FIGS. 1-9, the needle 3 is visible in the "before use" position of the needle shield 8. The needle 3 is also guided from the "before use" position of the needle shield 8 to the "in use" position of the needle shield 8. The needle 3 is therefore protected during this step and it is rendered more rigid, therefore allowing a safe and controlled injection.

On FIG. 10 is shown an alternative embodiment of the tube 20 of FIG. 3. On FIG. 10, is shown a tube 32 which is provided with an asymmetrical outer flange 33, the proximal face 34 of which is inclined so that said flange 33 is thicker in its part which is in alignment with a longitudinal cut 35 obtained as described for the longitudinal cut 21 of the tube 20 of FIG. 2. In consequence, in the "before use" and "in use" positions, the proximal face of the outer flange 33 is in contact with the distal plane surface 7 of the rim 6 of the support 2 only by its extremity located in alignment with the longitudinal cut 35. Once the needle shield 8 is in its "after use" position and the tube 32 is no more surrounded by the needle shield 8, the proximal face 34 of the outer flange 33 tends to come in tighter contact with the distal plane surface 7 of the rim 6 and the tube 32 cants as already described for tube 20 on FIGS. 1-9. The distal end 32b of the tube 32 comes in regard to the proximal end 8a of the needle shield 8 and the needle shield 8 is locked in its "after use" position.

On FIG. 11 is shown the assembling of the tube 20 and the helical spring 24 of the injection device 100 of embodiment of FIGS. 1-9. As can be seen on this figure, the tube 20 and the helical spring 24 can be preassembled, thereby forming a subset that can then subsequently be assembled on the needle 3 via a lever 300. The injection device 100 is therefore very easy to manufacture.

On FIGS. 12-16 is shown an alternative embodiment of the needle protection assembly of FIGS. 1-9 in which the cam is provided on the locking element.

The references designating the same elements as in FIGS. 1-9 have been maintained.

In reference to FIG. 12 is shown a needle protection assembly 1 according to the invention, in the "before use" position, mounted on an injection device 100 (partially shown). The needle protection assembly 1 of the invention comprises a support 2 that bears a needle 3. The support 2 comprises an inner core 4, and a proximal part 5 of outer diameter larger than the outer diameter of the inner cord 4 and forming with respect to said inner core 4 a rim 6. The rim 6 defines a plane surface 7 perpendicular to the longitudinal axis of the support 2. The support 2 is fixed to a barrel 25 intended to receive a product to be injected.

The needle protection assembly 1 of FIG. 12 also comprises a needle shield 36 receiving at least partially said support 2 and in particular said inner core 4 of said support 2. The needle shield 36 has the global shape of a tube having a longitudinal axis A'. The needle shield 36 is open at its proximal end 36a and at its distal end 36b. The inner wall of the needle shield 36 is provided with at least one peg 37 projecting inwardly and radially.

The needle protection assembly 1 of FIG. 1 further comprises a supporting element under the form of a tube 38 surrounding the inner core 4 of the support 2, said tube 38 being partly received within said needle shield 36. With reference to FIG. 13, the tube 38 has a longitudinal axis B' and is open at its proximal end 38a and at its distal end 38b. As appears on FIG. 13, a part of the wall of the tube 38 has been cut along a longitudinal plane, thereby defining an open longitudinal cut 39. As for tube 20 described on FIG. 2, the longitudinal cut 39 extends from a point 39a (visible on FIG. 12) located distally with respect to the proximal end 38a of the tube 38 up to the distal end 38b of the tube 38. The tube 38 is provided at its proximal end 38a with an asymmetrical outer flange 40, said outer flange 40 being provided on its proximal face with an inclined surface 41, of the same shape as the inclined surface 34 described for tube 32 of FIG. 10. In consequence, as can be seen on FIG. 12, the flange 40 is thicker in its part being in alignment with the longitudinal cut 39.

With reference to FIG. 13, the outer wall of the tube 38 is provided with a cam 42 diametrically opposing the longitudinal cut 39. The cam 42 comprises a first longitudinal track 43 and a second longitudinal track 44 substantially parallel to each other and separated by a separation wall 45. The first and second longitudinal tracks (43, 44) are joined at their respective proximal ends via an intersection 46. In the vicinity of the intersection 46, the first longitudinal track 43 is provided with a ramp 47, the distal end of which is provided with an inclined surface 48, the inclined surface 48 facing the second longitudinal track 44. In addition, the first longitudinal track 43 is provided with a step 49, located distally with respect to said ramp 47. The second longitudinal track 44 extends distally until the distal end 38b of the tube 38.

As will appear clearly from the description of FIGS. 12-16, the needle shield 36 is axially movable with respect to the tube 38 between a "before use" position, in which said needle shield 36 leaves a "before use" portion of the needle 3 uncovered, the needle 3 being visible by the user as shown on FIG. 12, an "in use" position in which said needle shield 36 leaves a "in use" portion of said needle 3 uncovered, the "in use" position being greater than the "before use" portion, as shown on FIG. 14, and an "after use" position in which said needle shield 36 covers said needle 3, as shown on FIGS. 15 and 16.

With reference to FIG. 12, in the "before use" position of the needle shield 36, the tube 38 is received within the needle shield 36 and the proximal face 38a of the tube 38 bears on the distal plane surface 7 defined by the rim 6 of the support 2 by means of the thicker part of the outer flange 40 bearing on the distal surface 7 of the rim 6 of the support 2. As appears also from FIG. 1, in this position, the tube 38 is maintained coaxial with the needle shield 36 because it is surrounded by the needle shield 36 which is tubular. In consequence, the respective longitudinal axis A' and B' of the needle shield 36 and of the tube 38 are merged. Part of the inclined surface 41 of the outer flange 40 which is diametrically opposed to the thicker part does not contact the distal plane surface 7 of the rim 6 as is shown on FIG. 12. As a remark, on this figure, the longitudinal axis A' and B' are also merged with the longitudinal axis of the injection device 100. In other words, the needle shield 36 and the tube 38 are in alignment with each other.

With reference to FIG. 12, the needle protection assembly 1 of FIG. 12 further comprises an outer sleeve 50 which receives the needle shield 36. The outer sleeve 50 is fixed to the barrel 25.

The needle protection assembly 1 of FIG. 12 further comprises a helical spring 51, located between the needle shield 36 and the tube 38. On the example shown on FIG. 12, the proximal end of the helical spring 51 bears on the distal face of the outer flange 40 of the tube 38 and its distal end bears on the proximal end 36a of the needle shield 36. In the "before use" position shown on FIG. 12, the helical spring 51 is in a partially expanded state. As will appear later in the detailed description of the operation of the injection device 100, the helical spring 51 acts as urging means for displacing the needle shield 36 from its "in use" position to its "after use" position.

The operation of the needle protection assembly 1 and of the injection device 100 will now be explained in reference to FIGS. 12 to 16.

On FIG. 12, the needle protection assembly 1 is in a "before use" position, the needle shield 8 covers part of the needle 3. Therefore, the needle 3 is visible for the user. The user can prick the needle 3 in the site of injection.

In this "before use" position, in reference with FIGS. 12 and 13, the peg 37 of the needle shield 36 is in an initial position located between the ramp 47 and the step 49 of the first track 43 of the cam 42 of the tube 38. The distal movement of the peg 37 is therefore prevented by the step 49.

In this "before use" position shown on FIG. 12, the longitudinal axis A' of the needle shield 36 and the longitudinal axis B' of the tube 38 are merged. The needle shield 36 and the tube 38 are in alignment with each other.

The user then applies the injection device 100 on the skin of a patient (not shown), inserts the needle 3 into the injection site until the distal end 36b of the needle shield 36 comes in contact with the skin. In order to fully insert the needle 3 in the site of injection, the user then exerts a distal pressure on the injection device 100, this having as a consequence to cause the distal movement of the outer sleeve 50 with respect to the needle shield 36, as shown on FIG. 14, said needle shield 36 being blocked against the skin of the patient (not shown). During the distal movement of the outer sleeve 50, the support 2, which is fixed to the outer sleeve 50, has also moved distally and has pushed the tube 38 in the distal direction via the rim 6 contacting the thicker part of the outer flange 40 of the tube 38. The needle shield 36 being stopped against the skin of the patient, the helical spring 51 is now in a more compressed state than in the before use position, as shown on FIG. 4. During the distal movement of the tube 38 with respect to the needle shield 36, the peg 37 has overcome the ramp 47 (see FIG. 13) and is now in abutment against the distal face of the intersection 46 of the first and second longitudinal tracks (43, 44) of the cam 42. The needle shield 36 is now in its "in use" position. The user may then realize the injection of the product to be injected.

In this "in use" position of the needle shield 36 as shown on FIG. 14, the longitudinal axis A' of the needle shield 36 and the longitudinal axis B' of the tube 38 are merged. The needle shield 36 and the tube 38 are in alignment with each other.

Once the injection step (not shown) is completed, the user releases its distal pressure on the injection device 100 and removes the injection device 100 from the injection site and the needle shield 36 is no more blocked by the skin of the patient. The helical spring 51 is therefore free to return to its expanded state and it causes the distal movement of the needle shield 36 with respect to the support 2 and to the tube 38 as shown on FIG. 15.

In reference with FIG. 13, the peg 37 (not shown) of the needle shield 36 is guided into the second track 44 of the cam 42 by the inclined surface 48. The peg 37 then travels all along the second longitudinal track 44 and escapes the second longitudinal track 44 together with the tube 38, as shown on FIG. 15, until it reaches it final position, corresponding to the "after use" position of the needle shield 36. As appears from FIG. 15, the final position of the peg 37 is therefore distally spaced with respect to its initial position.

The needle shield 36 therefore deploys and covers the needle 3, thereby preventing any accidental needle stick injury for the user and any re-use of the injection device 100. During this step, the helical spring 51 acts as urging means tending to displace the needle shield 36 from its "in use" position to its "after use" position.

While expanding, the helical spring 51 has pushed the needle shield 36 distally beyond the tube 38 which is then no more surrounded by the needle shield 36, as shown on FIG. 15, at the moment the needle shield 36 reaches its "after use" position". In consequence, the tube 38 is no more maintained coaxial with the needle shield 36. Thanks to the longitudinal cut 39 and to the inclined surface 41 of the outer flange 40 tending to be in tighter contact with the distal plane surface 7 of the rim of the support 2, the tube 38 naturally cants, as shown on FIG. 16 and its distal end 38b comes in regard to the proximal end 36a of the needle shield 36. The tube 38 is no more coaxial with the needle shield 36. This can be seen on FIG. 16 on which the longitudinal axis A' of the needle shield 36 and the longitudinal axis B' of the tube 38 intersect and are now forming an angle α'. The tube 38 therefore acts as a locking element of the needle shield 36 and is in a "locking position" when the needle shield 36 is in its "after use" position. As is visible from FIGS. 12 and 14, in the "before use" and "in use" positions of the needle shield 36, the tube 38 remained coaxial with the needle shield 36 and did not prevent movement of said needle shield 36 from a position to the other. On these FIGS. 12 and 14, the locking element formed by the tube 38 was in a "free position".

In all embodiments of the needle protection assembly of the invention described hereinabove, the locking element is not formed by the cooperation of the peg and the cam: this allows the urging means, used to cause the distal movement of the needle shield at the end of injection, to be low duty and not to have too high a force, therefore avoiding deformation of parts forming the needle protection assembly.

The invention claimed is:

1. Needle protection assembly intended to protect the needle of a needle assembly, said needle protection assembly comprising at least: a supporting element and a needle shield, said needle shield being axially movable with respect to said supporting element between an "in use" position in which said needle shield is intended to leave an "in use" portion of said needle uncovered, and an "after use" position distally spaced apart from said "in use" position and in which said needle shield is intended to cover said needle, said needle protection assembly further comprising:
at least one locking element located within said needle protection assembly and not accessible to the user, said locking element being movable between at least a "free" position, in which said needle shield can be moved at least from its "in use" position to its "after use" position, and a "locking" position, in Which said locking element prevents said needle shield from moving back from its "after use" position in the proximal direction,
urging means intended to displace said needle shield from its "in use" position to its "after use" position,
a peg located on said supporting element or on said needle shield, and a cam located on the other of said needle shield or on said supporting element, said peg being movable within said cam so as to define said "in use" and "after use" positions, upon increased or released distal pressure exerted by the user on said needle protection assembly, and
said locking element being not formed by said peg and said cam, wherein said needle shield having a longitudinal axis, said locking element has a general longitudinal shape having a longitudinal axis, the longitudinal axis of said needle shield and the longitudinal axis of said locking element are merged when said needle shield is in the "in use" position, said longitudinal axis of said needle shield forms an acute angle with the longitudinal axis of said locking element when said needle shield is in its "after use" position,
wherein said locking element has the global shape of a tube provided at its proximal end with an asymmetrical outer flange, and
wherein a longitudinal cut is formed in a distal end of said tube and which extends proximally therefrom, a thickened portion of said outer flange being in alignment with said longitudinal cut.

2. Needle protection assembly according to claim 1, wherein said needle shield is axially movable between a "before use" position, in which said needle shield leaves a "before use" portion of said needle uncovered, and said "in use" position, said "in use" portion being greater than said "before use" portion.

3. Needle protection assembly according to claim 2, wherein said cam includes at least a first and a second longitudinal tracks, both having a globally longitudinal shape and joining at an intersection via their respective proximal ends, respectively via their respective distal ends, said peg being located at an initial position in said first longitudinal track when said needle shield is in its before use position, and said peg being located at a "final" position in said second longitudinal track or beyond said second longitudinal track, when said needle shield is in said "after use" position, said "final" position of said peg being axially spaced with respect to said initial position.

4. Needle protection assembly according to claim 3, wherein said peg is located at said intersection of the first and second longitudinal tracks when said needle shield is in its "in use" position.

5. Needle protection assembly according to claim 3, wherein said cam is provided with an inclined surface at the vicinity of the intersection of said first and second longitudinal tracks, said inclined surface urging said peg in said second longitudinal track when said needle shield moves from its "in use" position to its "after use" position.

6. Needle protection assembly according to claim 1, wherein said supporting element is an outer sleeve receiving both said needle shield and said locking element.

7. Needle protection assembly according to claim 1, wherein said supporting element forms at least part of said locking element.

8. Needle protection assembly according to claim 1, wherein said outer flange is provided with a proximally-facing inclined surface.

9. Needle protection assembly according to claim 1, wherein said thickened portion of said outer flange is provided with one projection extending proximally.

10. Needle protection assembly according to claim 1, wherein said urging means comprise at least a helical spring.

11. Needle assembly comprising at least a needle hub provided with a needle wherein it further comprises a needle protection assembly according to claim 1.

12. Needle assembly according to claim 11, wherein said supporting element comprises said needle hub.

13. Injection device comprising at least a needle assembly and a reservoir, wherein it further comprises a needle protection assembly according to claim 1.

* * * * *